(12) United States Patent
Myung et al.

(10) Patent No.: US 9,194,963 B2
(45) Date of Patent: Nov. 24, 2015

(54) SCINTILLATING MODULE, POSITRON EMISSION TOMOGRAPHY, ION BEAM PROFILER, ION BEAM FILTER, AND ION BEAM GENERATING DEVICE USING SCINTILLATING MODULE

(71) Applicant: Electronics and Telecommunications Research Institute, Daejeon (KR)

(72) Inventors: Nam Soo Myung, Seongnam (KR); Moon Youn Jung, Daejeon (KR); Dong-Ho Shin, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 524 days.

(21) Appl. No.: 13/789,567

(22) Filed: Mar. 7, 2013

(65) Prior Publication Data
US 2013/0264484 A1 Oct. 10, 2013

(30) Foreign Application Priority Data

| Mar. 9, 2012 | (KR) | 10-2012-0024679 |
| Mar. 9, 2012 | (KR) | 10-2012-0024680 |
| Nov. 6, 2012 | (KR) | 10-2012-0124918 |
| Nov. 6, 2012 | (KR) | 10-2012-0124921 |

(51) Int. Cl.
*G01T 1/20* (2006.01)
*G01T 1/164* (2006.01)
*A61N 5/10* (2006.01)

(52) U.S. Cl.
CPC .............. *G01T 1/20* (2013.01); *A61N 5/1077* (2013.01); *G01T 1/164* (2013.01); *G01T 1/1642* (2013.01); *G01T 1/2006* (2013.01); *G01T 1/2008* (2013.01)

(58) Field of Classification Search
CPC ......... G01T 1/20; G01T 1/164; G01T 1/2006; A61N 5/1077
See application file for complete search history.

(56) References Cited

U.S. PATENT DOCUMENTS

| 3,032,657 | A | * | 5/1962 | Meier et al. ................. 250/486.1 |
| 4,677,299 | A | * | 6/1987 | Wong ......................... 250/363.03 |
| 4,942,302 | A | * | 7/1990 | Koechner ....................... 250/368 |
| 5,103,098 | A | * | 4/1992 | Fenyves ........................ 250/368 |
| 5,281,821 | A | * | 1/1994 | Antich et al. .................. 250/368 |
| 5,334,839 | A | * | 8/1994 | Anderson et al. ............. 250/368 |
| 5,382,798 | A | * | 1/1995 | Mouyen .................... 250/370.11 |
| 5,719,401 | A | * | 2/1998 | Chaney et al. ............. 250/370.1 |
| 6,255,655 | B1 | | 7/2001 | McCroskey et al. |
| 6,281,504 | B1 | | 8/2001 | Takayama et al. |
| 6,281,509 | B1 | * | 8/2001 | Ryan et al. .................... 250/397 |

(Continued)

OTHER PUBLICATIONS

Ingo Hofmann et al., "Collection and focusing of laser accelerated ion beams for therapy applications", Physical Review Special Topics—Accelerators and Beams, 2011, pp. 031304-1-031304-11, American Physical Society.

(Continued)

*Primary Examiner* — Marcus Taningco
*Assistant Examiner* — Djura Malevic

(57) ABSTRACT

A scintillating module is provided which includes a first scintillating layer including a plurality of scintillators extending in a first direction; a second scintillating layer including a plurality of scintillators extending in a second direction and stacked in a third direction with respect to the first scintillating layer, wherein the first, second and third directions are orthogonal to each other.

15 Claims, 14 Drawing Sheets

(56) References Cited

U.S. PATENT DOCUMENTS

| | | | |
|---|---|---|---|
| 6,407,392 B1 * | 6/2002 | Tsuyuki et al. | 250/368 |
| 6,710,349 B2 * | 3/2004 | Shao | 250/363.03 |
| 7,238,944 B2 * | 7/2007 | Bruder et al. | 250/367 |
| 7,274,020 B1 * | 9/2007 | Hindi et al. | 250/363.01 |
| 7,465,938 B1 * | 12/2008 | Hindi et al. | 250/390.11 |
| 7,667,203 B2 * | 2/2010 | Hindi et al. | 250/363.01 |
| 7,667,206 B1 * | 2/2010 | Hindi et al. | 250/390.07 |
| 8,063,379 B2 * | 11/2011 | Suhami | 250/370.09 |
| 8,436,312 B2 * | 5/2013 | Inadama et al. | 250/361 R |
| 2004/0114711 A1 * | 6/2004 | Ren et al. | 378/19 |
| 2004/0124360 A1 * | 7/2004 | Levin | 250/363.04 |
| 2004/0178347 A1 * | 9/2004 | Murayama et al. | 250/367 |
| 2006/0202125 A1 * | 9/2006 | Suhami | 250/368 |
| 2008/0210875 A1 * | 9/2008 | Hindi et al. | 250/363.01 |
| 2010/0288934 A1 * | 11/2010 | Keppel et al. | 250/362 |
| 2011/0057110 A1 * | 3/2011 | Testa et al. | 250/370.07 |
| 2012/0199740 A1 * | 8/2012 | Zeidler et al. | 250/310 |
| 2012/0205530 A1 * | 8/2012 | Beaulieu et al. | 250/252.1 |
| 2013/0032722 A1 * | 2/2013 | Szupryczynski et al. | 250/366 |

OTHER PUBLICATIONS

A Sam Beddar et al., "Plastic scintillation dosimetry: optimization of light collection efficiency", Phys. Med. Biol., 2003, pp. 1141-1152, IOP Publishing Ltd.

P. C. Rout et al., "A large area plastic scintillator detector array for fast neutron measurements", Preprint submitted to Nucl. Instr. And Meth. In Phys. Res. A, Sep. 4, 2008, pp. 1-27.

Victor Bom et al., "Real-time prompt gamma monitoring in spot-scanning proton therapy using imaging through a knife-edge-shaped slit", Physics in Medicine and Biology, Dec. 9, 2011, pp. 297-308, vol. 57, IOP Publishing.

* cited by examiner

SCINTILLATING MODULE, POSITRON EMISSION TOMOGRAPHY, ION BEAM PROFILER, ION BEAM FILTER, AND ION BEAM GENERATING DEVICE USING SCINTILLATING MODULE

CROSS-REFERENCE TO RELATED APPLICATIONS

A claim for priority under 35 U.S.C. §119 is made to Korean Patent Application No. 10-2012-0024680 filed Mar. 9, 2012, 10-2012-0024679 filed Mar. 9, 2012, 10-2012-0124921 filed Nov. 6, 2012 and 10-2012-0124918 filed Nov. 6, 2012, in the Korean Intellectual Property Office, the entire contents of which are hereby incorporated by reference.

BACKGROUND

The inventive concepts described herein relate to a scintillating module, position emission tomography, an ion beam profiler, an ion beam filter, and an ion beam generating device using the scintillating module.

A scintillating module may be a detector which electrically detects corpuscular radiation generated by accelerated particles. The scintillating module may include scintillating materials for detecting the corpuscular radiation. The scintillating module may convert energy of the corpuscular radiation penetrating the scintillating module into light. The light generated by the scintillating module may be concentrated to be converted into an electrical signal by a photoelectric conversion device.

In recent years, a positron emission tomography (PET) system or a single photon emission computerized tomography (SPECT) system may be mainly used for diagnosing of cancers and monitoring of radiation therapy. The PET system may use radioactive matters to take the inside of the body. The PET system may measure high energy of corpuscular radiation generated when generated positrons are annihilated by combination with electrons, using the scintillating module.

Meanwhile, radiation therapy (RT) may be widely used as oncotherapy. Radiation therapy may be therapy to kill tumors by directly applying radiation having high energy to the tumors. In particular, in comparison with a therapy technique using electromagnetic radiation such as X-ray, corpuscular radiation may enable radiation exposure to be remarkably reduced. However, fine control on energy magnitude and distribution of corpuscular radiation may be required to remove tumors using an ion beam, that is, the corpuscular radiation. To control an output of the corpuscular radiation, an ion beam generating device may accurately measure output corpuscular radiation using an ion beam profiler including a scintillating module.

SUMMARY

One aspect of embodiments of the inventive concept is directed to provide a scintillating module comprising a first scintillating layer including a plurality of scintillators extending in a first direction; a second scintillating layer including a plurality of scintillators extending in a second direction and stacked in a third direction with respect to the first scintillating layer, wherein the first, second and third directions are orthogonal each other.

In example embodiments, outer walls of the plurality of scintillators are formed to total reflect gamma rays.

In example embodiments, the scintillating layer includes a plurality of detectors which are configured to collect light generated from the plurality of scintillators and to output photoelectrons using the collected light.

In example embodiments, the plurality of scintillators has a triangular structure, a square pillar structure, a hexagonal structure, or a cylindrical structure.

Another aspect of embodiments of the inventive concept is directed to provide a positron emission tomography system comprising a scintillating module which generates light in response to a photon generated from radioactive substance; a photoelectric conversion module which converts the light into an electrical pulse; and an analysis module which calculates a position of the radioactive substance by analyzing the electrical pulse, wherein the scintillating module includes a plurality of scintillating layers stacked, the plurality of scintillating layers extends in a direction and includes a plurality of scintillators to generate the light in response to the photon, and extending directions of scintillators included in adjacent scintillating layers are orthogonal each other.

In example embodiments, the analysis module calculates incident energy of the photon using an integral value of the electrical pulse to a time and calculates a position of the radioactive substance using the calculated incident energy of the photon.

In example embodiments, the analysis module decides a scintillating layer, at which the photon gets out of existence, from among the plurality of scintillating layers using the electrical pulse and calculates a position of the radioactive substance using a position of the decided scintillating layer.

In example embodiments, the analysis module traces a progress course of the photon using the electrical pulse and calculates a position of the radioactive substance using the traced progress course of the photon.

In example embodiments, the analysis module measures a position of a detector, from which light is generated, and a light generation time using the electrical pulse and traces a progress course of the photon using the measured value.

Still another aspect of embodiments of the inventive concept is directed to provide an ion beam profiler comprising a scintillating module which generates light in response to an ion beam; a photoelectric conversion module which converts the light into an electrical pulse; and an analysis module which calculates energy distribution and progress course of the ion beam, wherein the scintillating module includes a plurality of scintillating layers stacked, the plurality of scintillating layers extends in a direction and includes a plurality of scintillators to generate the light in response to the ion beam, and extending directions of scintillators included in adjacent scintillating layers are orthogonal each other.

In example embodiments, the analysis module calculates incident energy of the ion beam using an integral value of the electrical pulse to a time and calculates the energy distribution and progress course of the ion beam using the calculated incident energy of the ion beam.

In example embodiments, the analysis module decides a scintillating layer, at which the ion beam gets out of existence, from among the plurality of scintillating layers using the electrical pulse and calculates the energy distribution and progress course of the ion beam using a position of the decided scintillating layer.

Still another aspect of embodiments of the inventive concept is directed to provide an ion beam filter comprising a scintillating module which generates light in response to a base ion beam and provides a collimated ion beam using the base ion beam; a photoelectric conversion module which converts the light into an electrical pulse; and an analysis module which calculates energy distribution and progress course of the ion beam, wherein the scintillating module includes a plurality of scintillating layers stacked and at least one hole, the plurality of scintillating layers extends in a direction and includes a plurality of scintillators to generate the light in response to the ion beam, extending directions of scintillators included in adjacent scintillating layers are orthogonal each other, and an energy distribution of the collimated ion beam is decided in response to the hole.

In example embodiments, the hole is formed from an incidence surface side of the scintillating module.

In example embodiments, the hole is formed from an output surface side of the scintillating module.

In example embodiments, the hole is formed inside the scintillating module.

In example embodiments, the energy distribution of the collimated ion beam is decided in response to a sum of a length of the at least one hole.

An ion beam generating device is provided which comprises an ion beam generator which generates a base ion beam by accelerating ions; and an ion beam filter which provides a collimated ion beam using the base ion beam. The ion beam filter comprises: a scintillating module which generates light in response to a base ion beam and provides a collimated ion beam using the base ion beam; a photoelectric conversion module which converts the light into an electrical pulse; and an analysis module which calculates energy distribution and progress course of the ion beam. The scintillating module includes a plurality of scintillating layers stacked and at least one hole, the plurality of scintillating layers extends in a direction and includes a plurality of scintillators to generate the light in response to the ion beam, extending directions of scintillators included in adjacent scintillating layers are orthogonal each other, and an energy distribution of the collimated ion beam is decided in response to the hole.

In example embodiments, the ion beam generator comprises a pulse laser which generates an ultra-short pulse laser; a pulse stretcher which stretches a pulse width of the ultra-short pulse laser; a pulse selector which selects a specific pulse of the stretched pulse laser; an amplifier which amplifies a magnitude of the selected pulse; and a pulse compressor which compresses a pulse width of the amplified pulse.

In example embodiments, the pulse selector includes a pockels cell.

BRIEF DESCRIPTION OF THE FIGURES

The above and other objects and features will become apparent from the following description with reference to the following figures, wherein like reference numerals refer to like parts throughout the various figures unless otherwise specified, and wherein.

DETAILED DESCRIPTION

Figure 1:
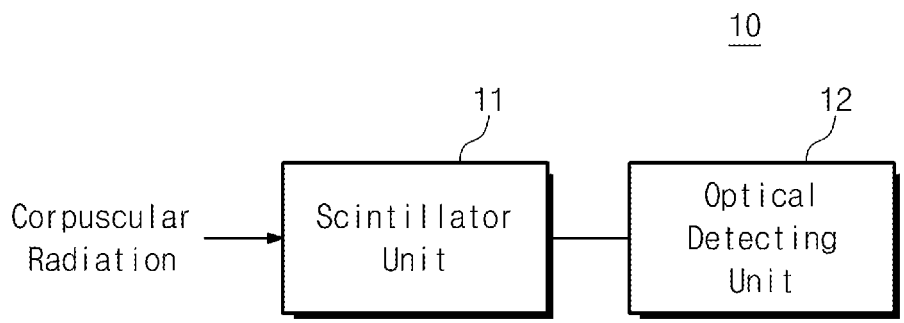
FIG. 1 is a block diagram schematically illustrating a scintillating module.

Embodiments will be described in detail with reference to the accompanying drawings. The inventive concept, however, may be embodied in various different forms, and should not be construed as being limited only to the illustrated embodiments. Rather, these embodiments are provided as examples so that this disclosure will be thorough and complete, and will fully convey the concept of the inventive concept to those skilled in the art. Accordingly, known processes, elements, and techniques are not described with respect to some of the embodiments of the inventive concept. Unless otherwise noted, like reference numerals denote like elements throughout the attached drawings and written description, and thus descriptions will not be repeated. In the drawings, the sizes and relative sizes of layers and regions may be exaggerated for clarity.

It will be understood that, although the terms "first", "second", "third", etc., may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the inventive concept.

Spatially relative terms, such as "beneath", "below", "lower", "under", "above", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" or "under" other elements or features would then be oriented "above" the other elements or features. Thus, the exemplary terms "below" and "under" can encompass both an orientation of above and below. The device may be otherwise oriented (rotated 90 degrees or at other orientations) and the spatially relative descriptors used herein interpreted accordingly. In addition, it will also be understood that when a layer is referred to as being "between" two layers, it can be the only layer between the two layers, or one or more intervening layers may also be present.

The terminology used herein is for the purpose of describing particular embodiments only and is not intended to be limiting of the inventive concept. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Also, the term "exemplary" is intended to refer to an example or illustration.

It will be understood that when an element or layer is referred to as being "on", "connected to", "coupled to", or "adjacent to" another element or layer, it can be directly on, connected, coupled, or adjacent to the other element or layer, or intervening elements or layers may be present. In contrast, when an element is referred to as being "directly on," "directly connected to", "directly coupled to", or "immediately adjacent to" another element or layer, there are no intervening elements or layers present.

Unless otherwise defined, all terms (including technical and scientific terms) used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and/or the present specification and will not be interpreted in an idealized or overly formal sense unless expressly so defined herein.

FIG. 1 is a block diagram schematically illustrating a scintillating module. Referring to FIG. 1, a scintillating module 10 may include a scintillator unit 11 and an optical detecting unit 12.

The scintillator unit 11 may include a plurality of scintillators. Corpuscular radiation generated by accelerated particles may be incident onto the scintillator unit 11. The input corpuscular radiation may cause Compton scattering via collision with an atom of a scintillator. With the Compton scattering, recoilelectron may be generated when corpuscular radiation collides with outer electrons of an atom included in a scintillator. The recoilelectron may have various kinetic energies according to energy and progress direction of input corpuscular radiation. The recoilelectron may do electrical reaction with another atom on a progress path. The recoilelectron may lose the kinetic energy by the electrical reaction and generate light via combination with an ionized atom. That is, the scintillator unit 11 may convert corpuscular radiation, which is generated from radioactive matter and is incident onto the scintillator unit 11, into light.

The optical detecting unit 12 may be coupled with the scintillator unit 11. The optical detecting unit 12 may include detectors respectively corresponding to scintillators. The optical detecting unit 12 may output a photoelectron by collecting lights generated from scintillators of the scintillator unit 11.

To measure corpuscular radiation accurately, a much amount of corpuscular radiation has to become incident onto the scintillator unit 11 and corpuscular radiation incident onto the scintillator unit 11 has to be detected accurately. In the scintillator unit 11, the amount of incidence and accuracy of detection may vary according to a structure of the scintillator unit 11. The structure of the scintillator unit 11 will be more fully described with reference to FIGS. 2 and 3.

Figure 2:
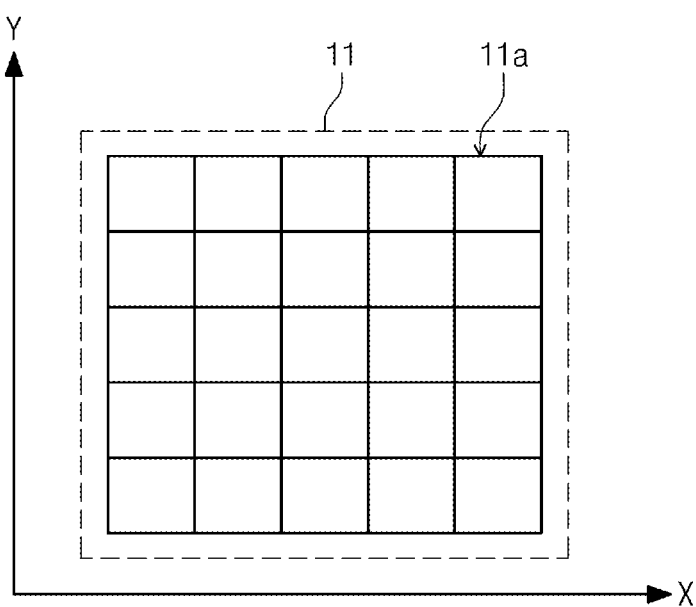
FIG. 2 is a front view of a scintillating module in FIG. 1.
Figure 3:
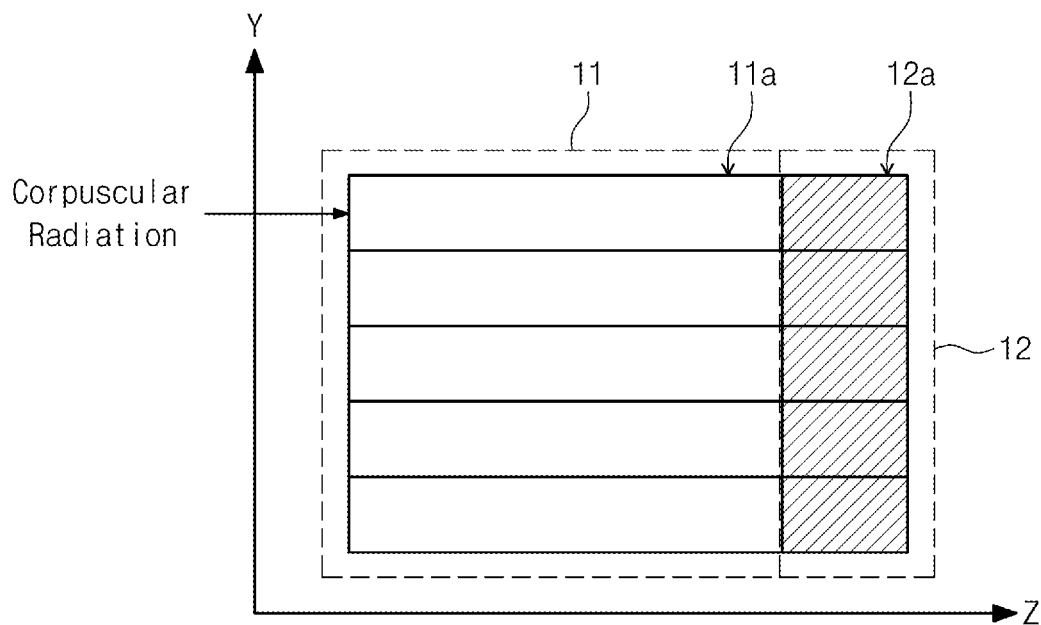
FIG. 3 is a lateral view of a scintillating module in FIG. 1.

FIG. 2 is a front view of a scintillating module in FIG. 1. FIG. 3 is a lateral view of a scintillating module in FIG. 1.

Referring to FIGS. 2 and 3, a scintillator unit 11 may be formed of a matrix of scintillators. The scintillators may be formed to have a square rod shape extending in a z-axis direction. Detectors may be connected to one ends of the scintillators, respectively. For ease of description, a first scintillator 11a and a first detector 12a connected thereto will be described. The remaining scintillators may be formed the same as the first scintillator 11a, and the remaining detectors may be formed the same as the first detector 12a.

It is assumed that corpuscular radiation is incident onto the first scintillator 11a. Light may be generated inside the first scintillator 11a by the corpuscular radiation incident onto the first scintillator 11a. The light generated may be collected to the first detector 12a from the inside of the first scintillator 11a.

The strength of the corpuscular radiation incident onto the first scintillator 11a may be calculated in response to the strength of light collected at the first detector 12a. A three-dimensional position of a radioactive matter may be calculated by three-dimensionally analyzing the strength of the corpuscular radiation and an XY coordinate of a scintillator from which corpuscular radiation is detected.

However, the corpuscular radiation may not be vertically incident onto a surface of the scintillator unit 11. For example, the corpuscular radiation may be obliquely incident onto a surface of the scintillator unit 11, so that scintillation is generated from plural scintillators. Since scintillators extend in the z-axis direction, the probability that the corpuscular radiation penetrates an outer wall of a scintillator onto which it is first incident may be high. Also, recoilelectron generated at one scintillator may be transferred to an adjacent scintillator over an outer wall of a scintillator.

Figure 4:
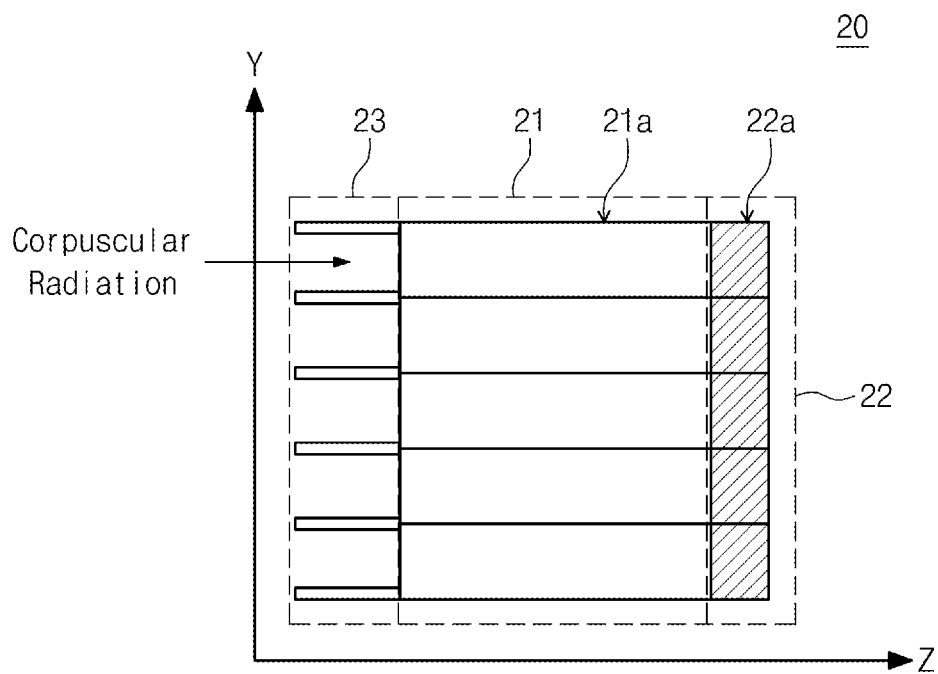
FIG. 4 is a lateral view of a scintillating module according to another embodiment of the inventive concept.

FIG. 4 is a lateral view of a scintillating module according to another embodiment of the inventive concept. A scintillating module 20 may be the same as a scintillating module 10 in FIG. 1 except that a guide unit 23 is added.

The guide unit 23 may absorb corpuscular radiation obliquely incident onto an XY surface of a scintillator unit 21. Alternatively, the guide unit 23 may change a progress angle of corpuscular radiation obliquely incident onto the XY surface of the scintillator unit 21. That is, the guide unit 23 may enable the corpuscular radiation to be vertically incident onto the XY surface of the scintillator unit 21. The guide unit 23 may include a plurality of collimators or pinholes.

The guide unit 23 of the scintillating module 20 may prevent recoilelectron or corpuscular radiation from being penetrated between scintillators. Thus, the scintillating module 20 may prevent an error due to interference between scintillators.

Figure 5:
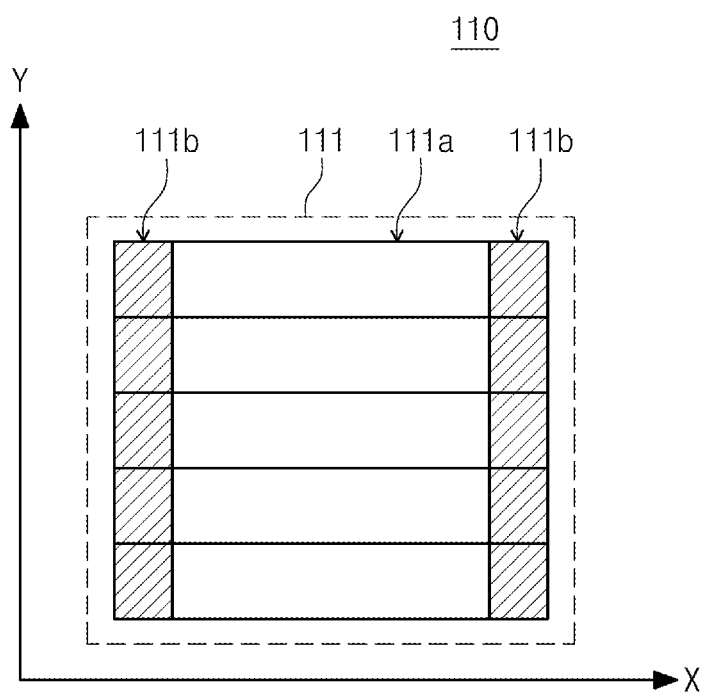
FIG. 5 is a front view of a scintillating module according to still another embodiment of the inventive concept.
Figure 6:
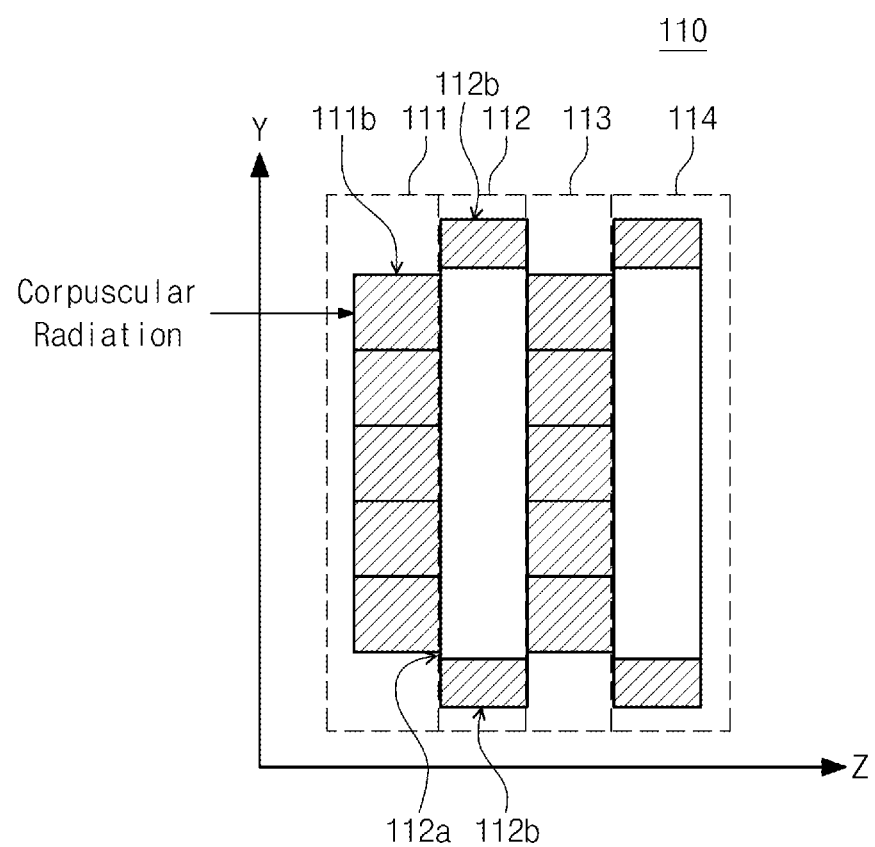
FIG. 6 is a lateral view of a scintillating module in FIG. 5.
Figure 7:
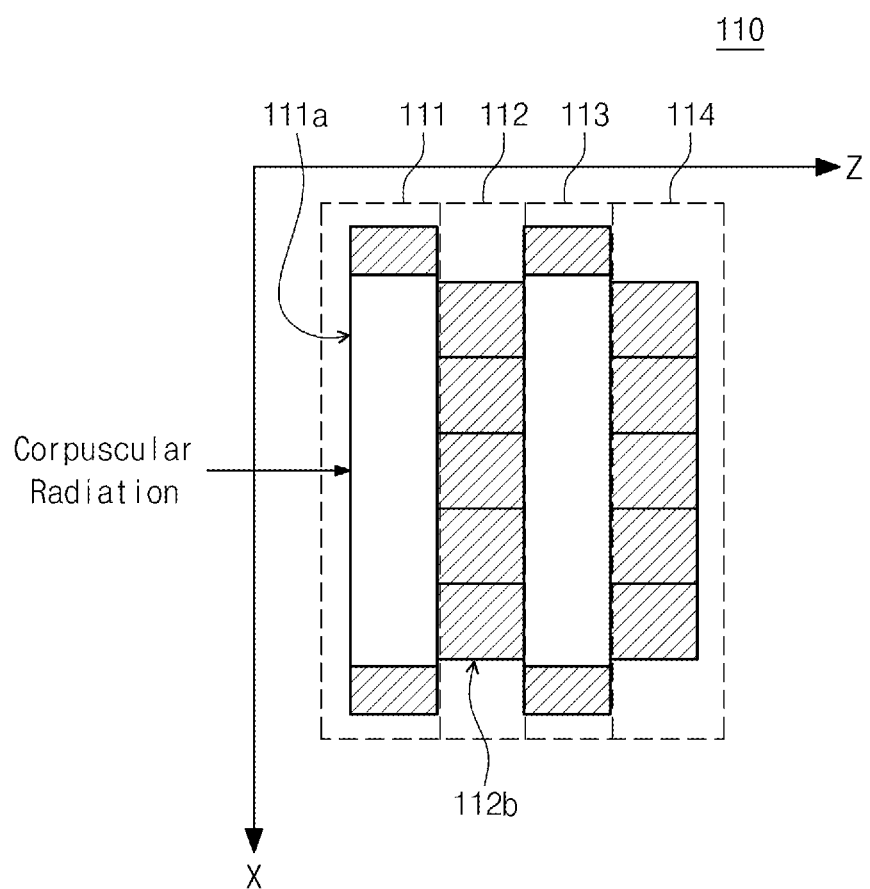
FIG. 7 is a top view of a scintillating module in FIG. 5.

FIG. 5 is a front view of a scintillating module according to still another embodiment of the inventive concept. FIG. 6 is a lateral view of a scintillating module in FIG. 5. FIG. 7 is a top view of a scintillating module in FIG. 5.

Referring to FIGS. 5 to 7, a scintillating module 110 may be formed of a plurality of scintillating layers 111 to 114 which are stacked. In example embodiments, there is illustrated an example in which four scintillating layers are stacked. However, the inventive concept is not limited thereto.

The scintillating layers 111 to 114 may include a plurality of scintillators arranged in line. As illustrated in FIGS. 5 to 7, scintillators included in each of the scintillating layers 111 to 114 may extend in a direction being at right angles to scintillators included in adjacent scintillating layers.

In example embodiments, cross sections of scintillators may be illustrated to be square. However, the inventive concept is not limited thereto. For example, cross sections of scintillators may be formed to have various shapes including a circle, a regular hexagon, and a regular triangle.

Based on a plurality of scintillating layers stacked in an orthogonal direction, the scintillating module 110 may measure the strength and progress direction of corpuscular radiation regardless of an incidence angle of the corpuscular radiation. That is, the scintillating module 110 may not limit the field of view of each of the scintillating layers 111 to 114.

The scintillating module 110 may use all corpuscular radiation for measurement without selectively penetrating corpuscular radiation. In comparison with the case that a part of corpuscular radiation is selectively used, the scintillating module 110 may provide high resolution of measurement using a less amount of radioactive matter.

The scintillating module 110 may correct interference between scintillators using a plurality of layers. Since the scintillating module 110 does not prevent interference between scintillators using a size of a cross section of a scintillator, a cross section of the scintillator may be realized to be small. This may mean that the resolution of the scintillating module 110 is further improved.

For ease of description, a first scintillator 111a of a first scintillating layer 111 and a second scintillator 112a of a second scintillating layer 112 will be described. The remaining scintillating layers and scintillators may be configured the same as will be described below.

A first scintillating layer 111 may be formed of scintillators having a rod shape extending in an X-axis direction and detectors connected thereto. For example, first detectors 111b may be connected to both ends of the first scintillator 111a.

A second scintillating layer 112 may be formed of scintillators having a rod shape extending in a Y-axis direction and detectors connected thereto. For example, second detectors 112b may be connected to both ends of the second scintillator 112a.

A boundary interface between adjacent scintillators may be formed such that the total reflection on light is easy. That is, scintillation generated in a scintillator may be collected at both ends of the scintillator by the total reflection, not transferred to an adjacent scintillator.

If corpuscular radiation is generated by radioactive matter or accelerated particle, it may be incident onto the first scintillating layer 111. Since the corpuscular radiation progresses in a Z-axis direction, it may get out of existence after penetrating a plurality of scintillating layers in proportion to the strength of the corpuscular radiation. In example embodiments, it is assumed that corpuscular radiation is incident onto a first scintillating layer and a second scintillating layer, that is, a first scintillator 111a and a second scintillator 112a thereof.

The corpuscular radiation may generate light over passing the first scintillator 111a. The light generated from the scintillator 111a may be collected by the first detectors 111b at both ends of the first scintillator 111a by the total reflection.

Also, the corpuscular radiation incident onto the second scintillator 112a may generate light and then dissipate. The light generated from the scintillator 112a may be collected by the second detectors 112b at both ends of the second scintillator 112a by the total reflection.

The incidence strength of corpuscular radiation incident onto the first scintillator 111a may be calculated in response to the strength of light collected at the first detectors 111b. The incidence strength of corpuscular radiation incident onto the second scintillator 112a may be calculated in response to the strength of light collected at the second detectors 112b.

The scintillating module 110 may calculate an XY coordinate, at which corpuscular radiation is detected, using position information of scintillators of each scintillating layer from which corpuscular radiation is detected.

Since including a plurality of scintillating layers 111 to 114, the scintillating module 110 may calculate a progress direction of corpuscular radiation using position information of scintillators of each scintillating layer from which corpuscular radiation is detected.

That is, unlike assumption that corpuscular radiation is incident onto a scintillator like a scintillating module 11 in FIG. 2, the scintillating module 110 may trace corpuscular radiation passing through a plurality of scintillators, so that a size of a cross section of a scintillator is reduced in comparison with the scintillating module 11. Also, it is possible to improve the resolution. In addition, the scintillating module 110 may analyze the whole corpuscular radiation generated from radioactive matter regardless of an incidence angle of the corpuscular radiation.

Figure 8:
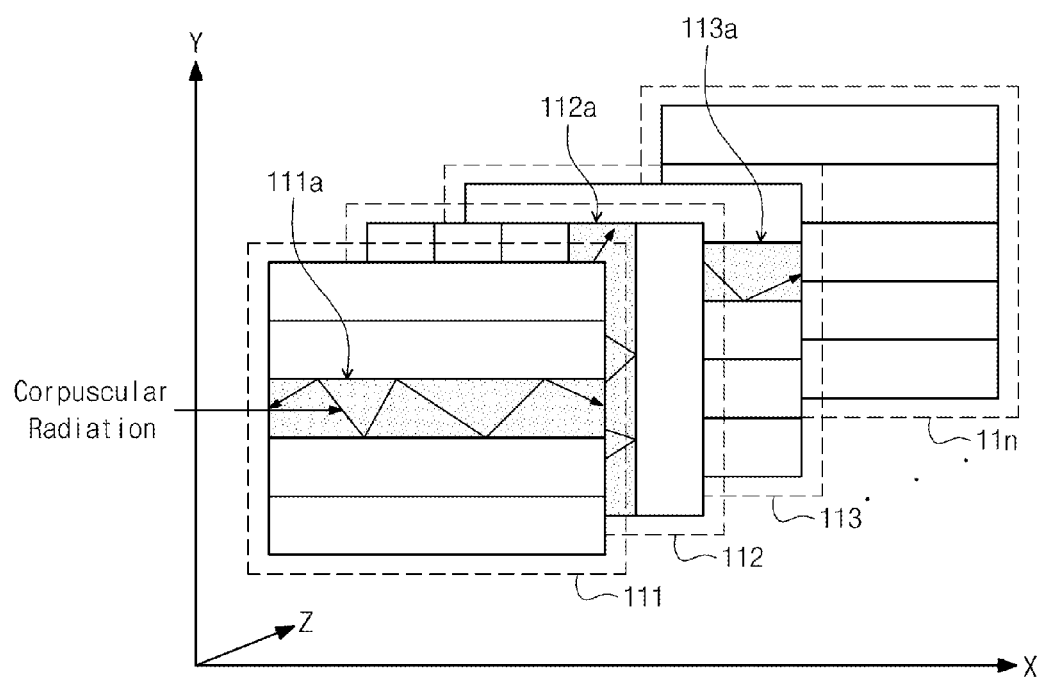
FIG. 8 is a block diagram schematically illustrating a part of a scintillating module in FIG. 5.

FIG. 8 is a block diagram schematically illustrating a part of a scintillating module in FIG. 5. Scintillators 111a, 112a, and 113a heavily marked may indicate scintillators onto which corpuscular radiation is incident. In FIG. 8, there are not illustrated detectors connected to both ends of respective scintillators.

Corpuscular radiation generated by radioactive matter or accelerated particle may be incident onto a scintillating module 110 with various energies and incidence angles. The input corpuscular radiation may penetrate scintillating layers 111 to 11n included in the scintillating module 110. The corpuscular radiation may lose energy due to collision whenever it passes through each scintillating layer. Energy which the corpuscular radiation loses may be converted into light by Compton scattering as described above.

If energy of the corpuscular radiation is lower than an energy barrier for penetrating a boundary interface between scintillating layers, the corpuscular radiation may dissipate without being incident onto a next scintillating layer. Thus, it is possible to calculate incident energy of corpuscular radiation using a scintillating layer from which light is lastly generated. Below, an operation of the scintillating module 110 will be more fully described with reference to accompanying drawings.

It is assumed that a third scintillating layer 113 is a scintillating layer at which corpuscular radiation dissipates. It is assumed that the corpuscular radiation passes through a first scintillator 111a of a first scintillating layer 111, a second scintillator 112a of a second scintillating layer 112, and a third scintillator 113a of a third scintillating layer 113 until it dissipates.

The corpuscular radiation may generate light over penetrating the first to third scintillators 111a, 112a, and 113a. Light generated in a scintillator may be collected at both ends of the scintillator by the total reflection.

The strength of light collected at both ends of the scintillator may be proportional to energy which corpuscular radiation loses over passing through a scintillator. The incident energy of the corpuscular radiation may be calculated by measuring the strength of light collected at the first to third scintillators 111a, 112a, and 113a.

Also, it is possible to trace a progress course of corpuscular radiation of XY coordinates of the first to third scintillators 111a, 112a, and 113a. For example, the third scintillator 113a may have a Y coordinate value larger than that of the first scintillator 111a. Thus, the corpuscular radiation may be traced to progress in a positive Y-axis direction and a positive Z-axis direction. As the number of scintillating layers through which the corpuscular radiation passes increases, a progress course of the corpuscular radiation may be traced exactly.

Figure 9:
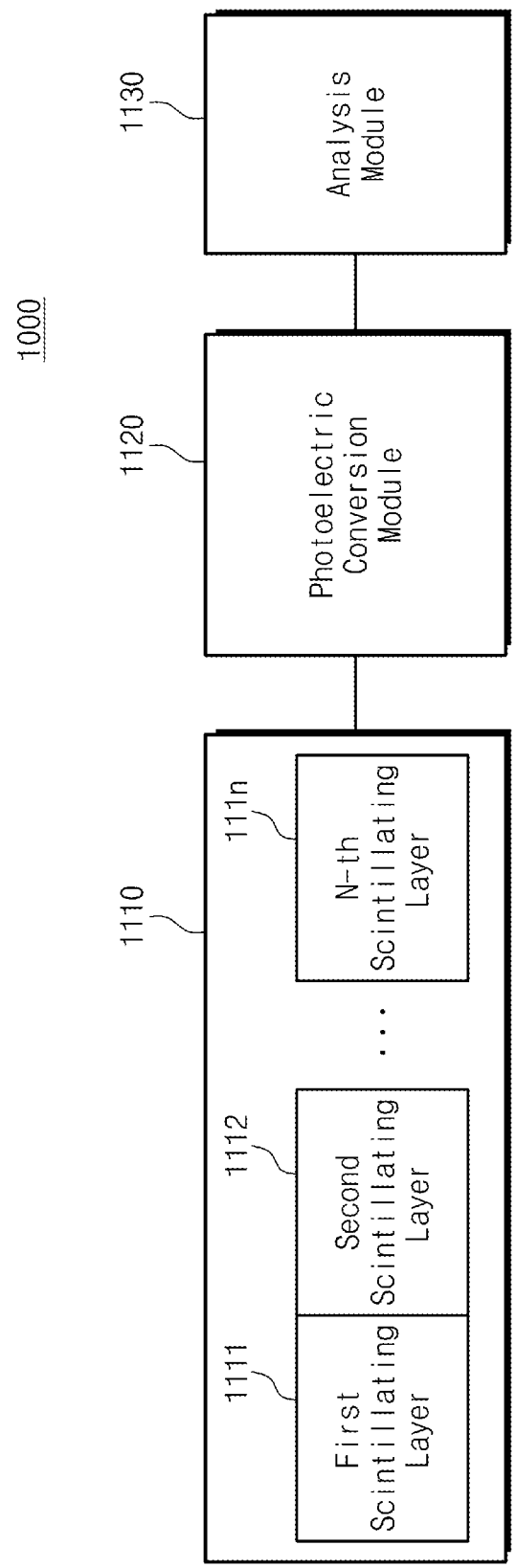
FIG. 9 is a block diagram schematically illustrating a positron emission tomography system to which a scintillating module of FIG. 5 is applied.

FIG. 9 is a block diagram schematically illustrating a positron emission tomography system to which a scintillating module of FIG. 5 is applied. Referring to FIG. 9, a positron emission tomography (PET) system may include a scintillating module 1110, a photoelectric conversion module 1120, and an analysis module 1130.

The scintillating module 1110 may include a plurality of scintillating layers 1111 to 111n, each of which includes a plurality of scintillators and detectors connected thereto. The scintillating module 1110 may output a photoelectron by converting a gamma ray generated from radioactive matter into light. The scintillating module 1110 may analyze the whole corpuscular radiation generated from radioactive matter regardless of an incidence angle of the corpuscular radiation, so that measurement is performed with a less amount of radioactive matter. Since typical radioactive matter is harmful to the body, the scintillating module 1110 may have such a merit that influence of the measurement on the boy is reduced.

The photoelectric conversion module 1120 may convert a photoelectron into a photo electric current pulse to amplify the converted pulse. The photoelectric conversion module 1120 may be a Photomultiplier tube (PMT). However, the inventive concept is not limited thereto.

The analysis module 1130 may calculate a three-dimensional position of radioactive matter by analyzing the photo electric current pulse from the photoelectric conversion module 1120. The analysis module 1130 may monitor photo electric current pulses generated from scintillators of the scintillating layers 1111 to 111n. An integral value of a photo electric current pulse generated from a scintillator may be proportional to energy lost at the scintillator. The analysis module 1130 may calculate a position of radioactive matter by measuring an integral value of a photo electric current pulse generated from each scintillator and simultaneously tracing a relative position and a start point of time when the photo electric current pulse is generated.

The analysis module 1130 may include an output unit. The output unit may be an image output device (e.g., a monitor). The analysis module 1130 may provide a user with the calculated position of radioactive matter using the output unit. A position of radioactive matter provided by the analysis module 1130 may include a three-dimensional image.

Figure 10:
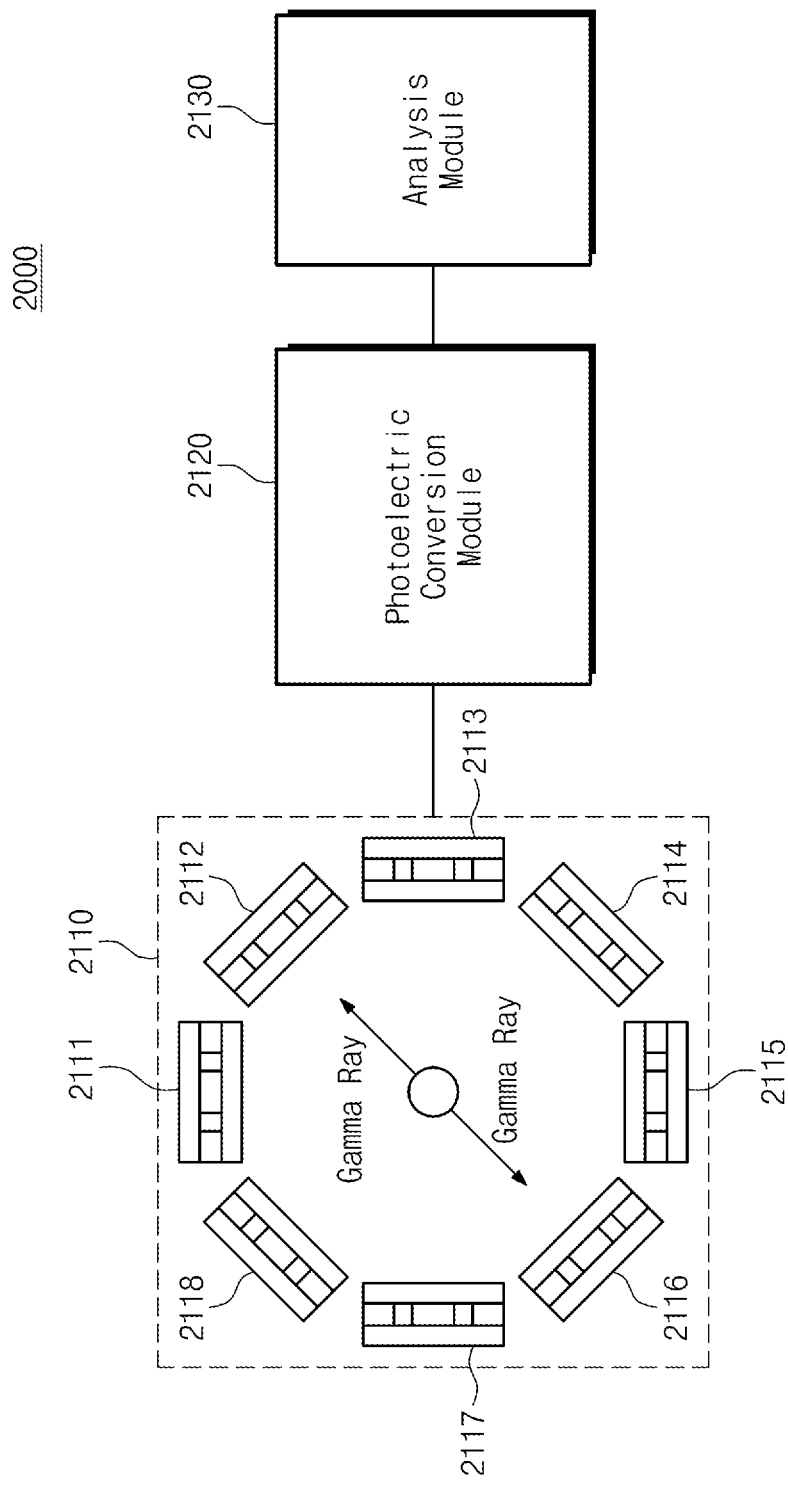
FIG. 10 is a block diagram schematically illustrating a positron emission tomography system according to another embodiment of the inventive concept.

FIG. 10 is a block diagram schematically illustrating a positron emission tomography system according to another embodiment of the inventive concept. Referring to FIG. 10, a positron emission tomography (PET) system may include a scintillating module group 2110, a photoelectric conversion module 2120, and an analysis module 2130. The photoelectric conversion module 2120 and the analysis module 2130 may be substantially the same as a photoelectric conversion module 1120 and an analysis module 1130 in FIG. 9.

The scintillating module group 2110 may include a plurality of scintillating modules 2111 to 2118, each of which is configured substantially the same as a scintillating module 110 in FIG. 5. Each of the scintillating modules 2111 to 2118 may include a plurality of scintillating layers, and scintillators included in adjacent scintillating layers are arranged to extend in an orthogonal direction. In FIG. 10, there is illustrated an example in which the scintillating module group 2110 includes eight scintillating modules. However, the inventive concept is not limited thereto.

The scintillating modules 2111 to 2118 may be arranged in a ring shape on the basis of a target to be measured. Alternatively, the scintillating modules 2111 to 2118 may be arranged to form an arc on the basis of a target to be measured so as to rotate on the basis of the target to be measured.

A corpuscular radiation pair (e.g., a gamma ray pair) generated from radioactive matter injected into the target to be measured, for example, the body may progress in opposite directions. Thus, two scintillating modules, for example, the second and sixth scintillating modules 2112 and 2116 may detect the gamma ray pair.

Radioactive matter used for measurement may be FDG (Fludeoxyglucose). The inventive concept may be described under the assumption that a gamma ray is generated from radioactive matter. However, sorts of radioactive matter used for measurement and sorts of a photo pair generated from the radioactive matter may not be limited to this disclosure.

Figure 11:
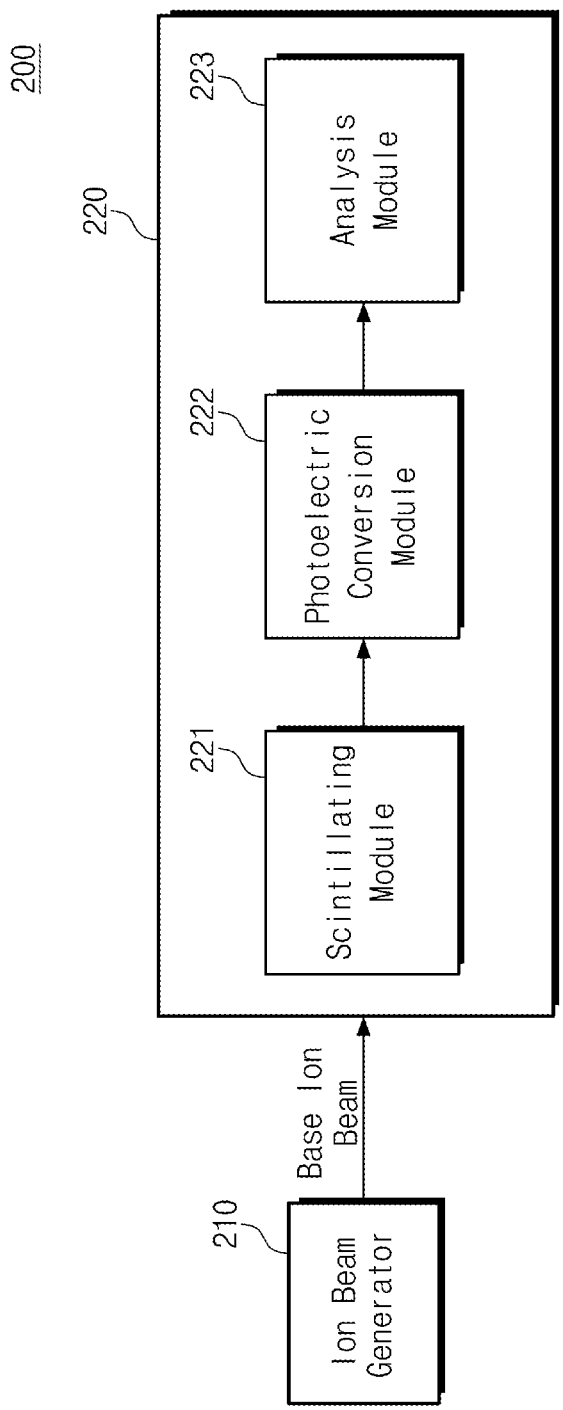
FIG. 11 is a block diagram schematically illustrating an ion beam profiler using a scintillating module of FIG. 5 and an ion beam generating device including the ion beam profiler.

FIG. 11 is a block diagram schematically illustrating an ion beam profiler using a scintillating module of FIG. 5 and an ion beam generating device including the ion beam profiler. The ion beam generating device 200 may include an ion beam generator 210 and an ion beam profiler 220.

The ion beam generating device 200 may monitor an ion beam generated from the ion beam generator 210 using the ion beam profiler 220. The ion beam generating device 200 may feed a monitoring result of the ion beam profiler 220 back to control an ion beam generated from the ion beam generator 210.

The ion beam generator 210 may generate collimated ion radiation, that is, an ion beam by accelerating an ion. The ion beam generator 210 may be a Cyclotron or Synchrotron particle accelerator. Alternatively, the ion beam generator 210 may accelerate an ion using a laser pulse. However, the inventive concept is not limited thereto.

The ion beam profiler 220 may monitor an ion beam generated from the ion beam generator 210. The ion beam profiler 220 may include a scintillating module 221, a photoelectric conversion module 222, and an analysis module 223. The ion beam profiler 220 may monitor energy distribution and progress course of the ion beam by measuring light generated when an ion beam passes through a plurality of scintillators. Below, the ion beam generator 210 and the ion beam profiler 220 will be more fully described with reference to FIG. 12.

Figure 12:
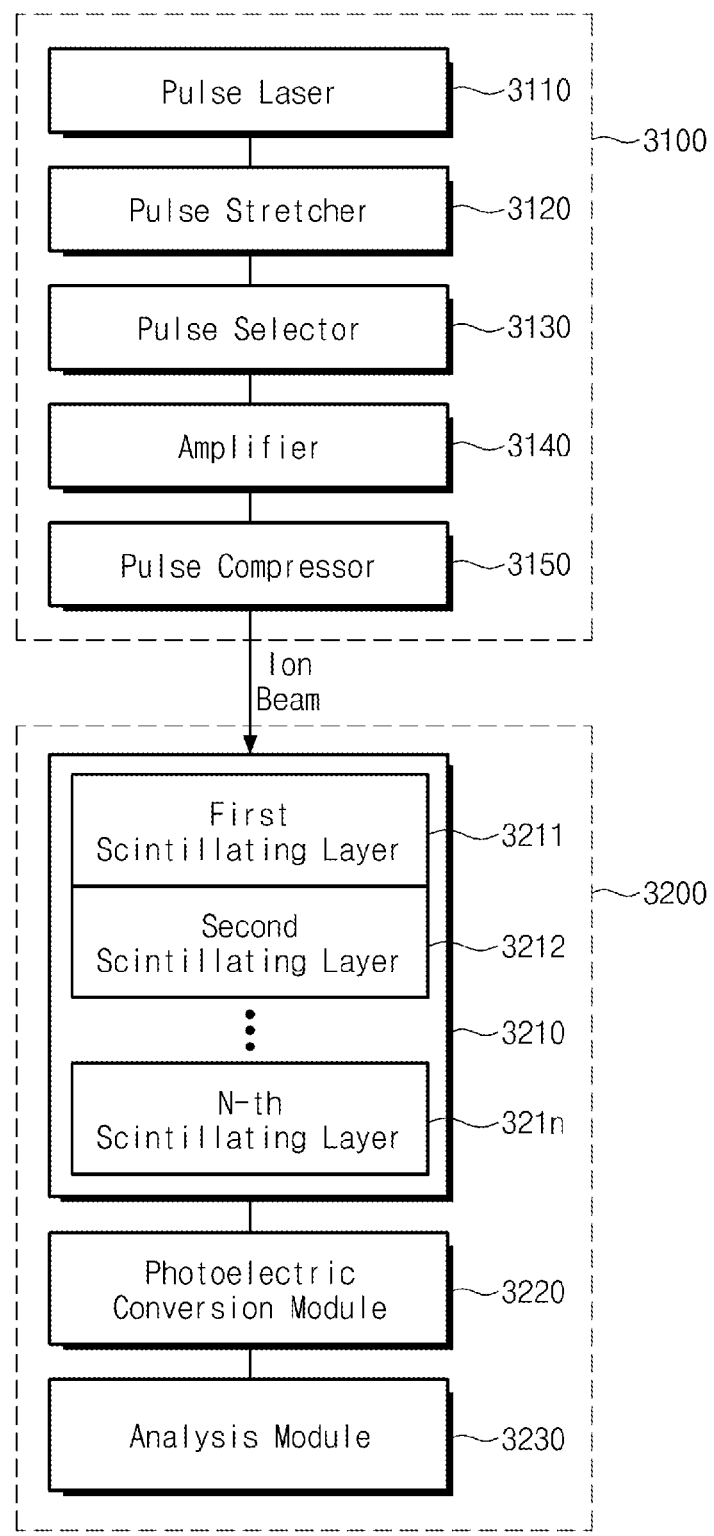
FIG. 12 is a block diagram schematically illustrating an ion beam generating device according to an embodiment of the inventive concept.

FIG. 12 is a block diagram schematically illustrating an ion beam generating device according to an embodiment of the inventive concept. Referring to FIG. 12, an ion beam generating device 3000 may include an ion beam generator 3100 and an ion beam profiler 3200.

The ion beam profiler 3200 may monitor energy and progress course of an ion beam using a plurality of scintillating layers. The ion beam generating device 3000 may control an ion beam generated from the ion beam generator 3100 using a monitoring result of the ion beam profiler 3200.

In FIG. 12, the ion beam generator 3100 may generate a high-power laser pulse using the chirped pulse amplification (CPA) technique. The ion beam generator 3100 may generate the ion beam by accelerating an ion using the high-power laser pulse. The ion beam generator 3100 may include a pulse laser 3110, a pulse stretcher 3120, a pulse selector 3130, an amplifier 3140, and a pulse compressor 3150.

The pulse laser 3110 may generate an ultra-short pulse laser. The pulse laser 3110 may be a mode-locked oscillator. Alternatively, the pulse laser 3110 may be a Ti-Sapphire laser. However, the inventive concept is not limited thereto.

The pulse stretcher 3120 may stretch a pulse width of the ultra-short pulse laser generated from the pulse laser 3110. The pulse stretcher 3120 may change a pulse width by performing optical dispersion on a course length of the ultra-short pulse laser using a variation in a refractive index of light according to a wavelength. The pulse stretcher 3120 may stretch a pulse width of the ultra-short pulse laser such that an instant maximum output of the ultra-short pulse laser is maintained low.

The pulse selector 3130 may select a pulse to be amplified of the stretched ultra-short pulse laser. The pulse selector 3130 may include a polarizing beam splitter (PBS). The pulse selector 3130 may further include a pockels cell. The pockels cell may be used as an optical shutter which is selectively turned on only when a pulse to be amplified is penetrated.

The amplifier 3140 may amplify a pulse selected by the pulse selector 3130. The amplifier 3140 may be configured to include a plurality of amplification states. Since an instant maximum output of the stretched pulse amplified by the amplifier 3140 is low, the stretched pulse may be amplified without damaging of optical medium in comparison with a short-wavelength pulse not stretched.

The pulse compressor 3150 may compress the amplified pulse to an original pulse width. The pulse compressor 3150 may include a plurality of diffraction grids. The pulse compressor 3150 may compress a pulse by diffracting the pulse using the plurality of diffraction grids. The pulse compressor 3150 may output an ultra-short pulse laser having an amplified output.

If the high-power ultra-short pulse laser from the pulse compressor 3150 is integrated at a thin film, the thin film may be ionized. Ions and electrons may be separated by ionization of the thin film. A strong electric field may be formed between the separated ions and electrons, and an ion accelerated by the electric field may be output as an ion beam.

The ion beam output from the pulse compressor 3150 of the ion beam generator 3100 may be monitored by the ion beam profiler 3200. The ion beam profiler 3200 may include a scintillating module 3210, a photoelectric conversion module 3220, and an analysis module 3230.

The ion beam profiler 3200 may monitor energy distribution and progress course of an ion beam using a plurality of scintillating layers 3211 to 321n. The ion beam profiler 3200 may provide a monitoring result to a user or feed it back to the ion beam generator.

The scintillating module 3210 may include a plurality of scintillating layers 3211 to 321n, each of which includes a plurality of scintillators and detectors connected thereto. The scintillating module 3210 may output a photoelectron by converting an ion beam into light.

The photoelectric conversion module 3220 may convert the photoelectron into a photo electric current pulse to amplify the converted pulse. The photoelectric conversion module 3220 may be a photomultiplier tube (PMT). However, the inventive concept is not limited thereto.

The analysis module 3230 may analyze the photo electric current pulse provided from the photoelectric conversion module 3220 to monitor the energy distribution and process course of the ion beam. The analysis module 3230 may monitor photo electric current pulses generated from scintillators.

An integral value of a photo electric current pulse generated from a scintillator may be proportional to energy lost at the scintillator. The analysis module 3230 may calculate the energy distribution and process course of the ion beam by measuring an integral value of a photo electric current pulse generated from each scintillator and simultaneously tracing a relative position and a start point of time when the photo electric current pulse is generated.

The analysis module 3230 may include an output unit. The output unit may be an image output device (e.g., a monitor). The analysis module 3230 may provide a user with the calculated energy distribution and process course of the ion beam using the output unit. The energy distribution and process course of the ion beam provided by the analysis module 3230 may include a three-dimensional image.

Figure 13:
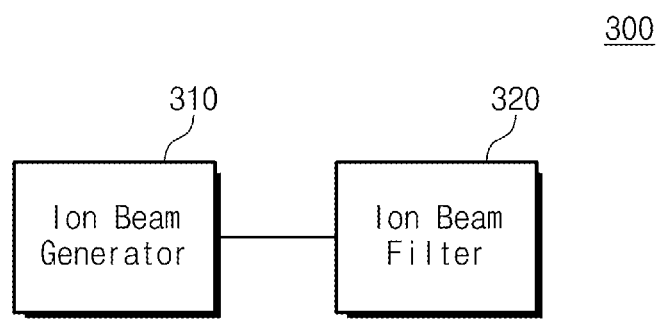
FIG. 13 is a block diagram schematically illustrating an ion beam generating device according to another embodiment of the inventive concept.

FIG. 13 is a block diagram schematically illustrating an ion beam generating device according to another embodiment of the inventive concept. Referring to FIG. 13, an ion beam generating device 300 may include an ion beam generator 310 and an ion beam filter 320. The ion beam generator 310 in FIG. 13 may be configured the same or substantially the same as an ion beam generator 210 in FIG. 11.

An ion beam generated from the ion beam generator 310 may have a wide angle of dispersion ranging from 1 to a dozen degree and a wide bandwidth ranging from several MeV to 200 MeV. The ion beam filter 320 may focus energy of an ion beam, generated from the ion beam generator 310, at a specific energy region using a plurality of scintillating layers. The ion beam generating device 300 may enable precise therapy by providing an ion beam focused using the ion beam filter 320.

The ion beam filter 320 may be configures the same as an ion beam profiler 310 in FIG. 11. Below, the ion beam filter 320 will be more fully described with reference to FIG. 14.

Figure 14:
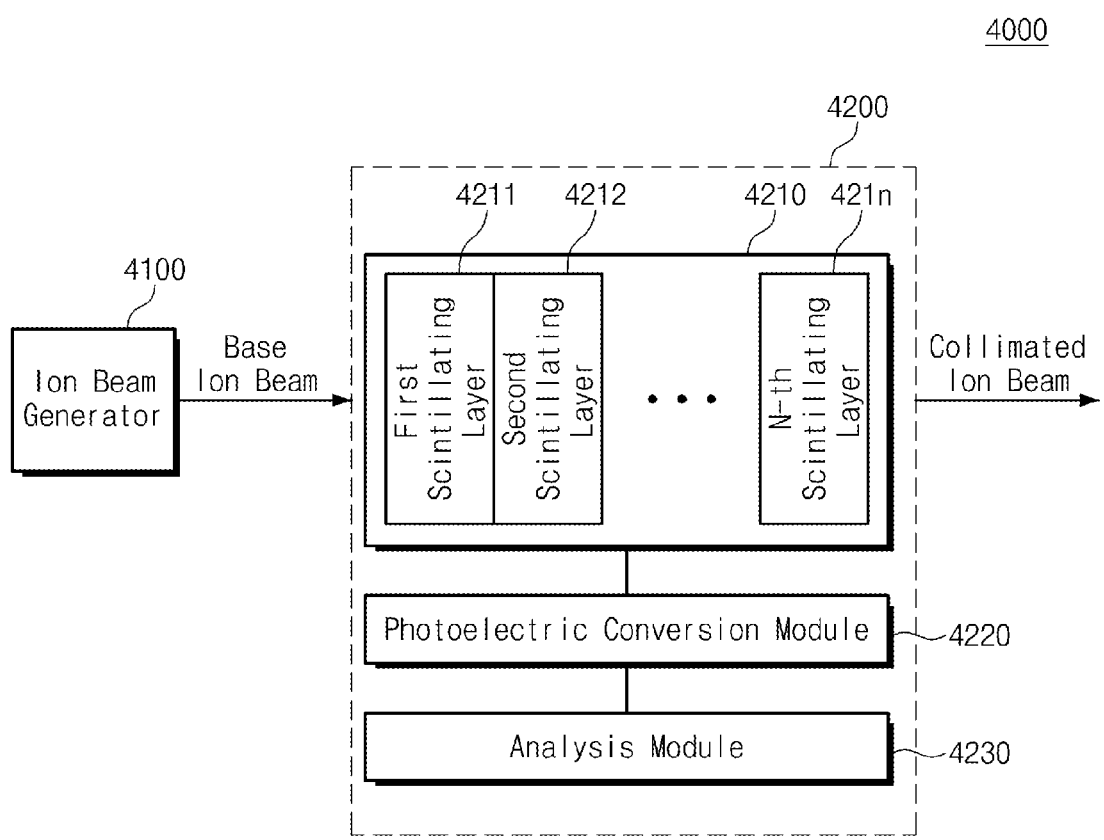
FIG. 14 is a block diagram schematically illustrating an ion beam generating device in FIG. 13.

FIG. 14 is a block diagram schematically illustrating an ion beam generating device in FIG. 13. Referring to FIG. 14, an ion beam generating device 4000 may include an ion beam generator 4100 and an ion beam filter 4200. The ion beam filter 4200 may include a scintillating module 4210, a photoelectric conversion module 4220, and an analysis module 4230.

The ion beam filter 4200 may monitor energy distribution and progress course of an ion beam using a plurality of scintillating layers 4211 to 421n. The ion beam filter 4200 may provide a monitoring result to a user or feed it back to the ion beam generator.

The ion beam filter 4200 may focus energy of an ion beam, generated from the ion beam generator 4100, at a specific energy region using a plurality of scintillating layers 4211 to 421n. The ion beam generating device 4000 may enable precise therapy by providing an ion beam focused using the ion beam filter 4200. Below, an ion beam focusing method of an ion beam filter 4200 will be more fully described with reference to FIGS. 15 to 18.

Figure 15:
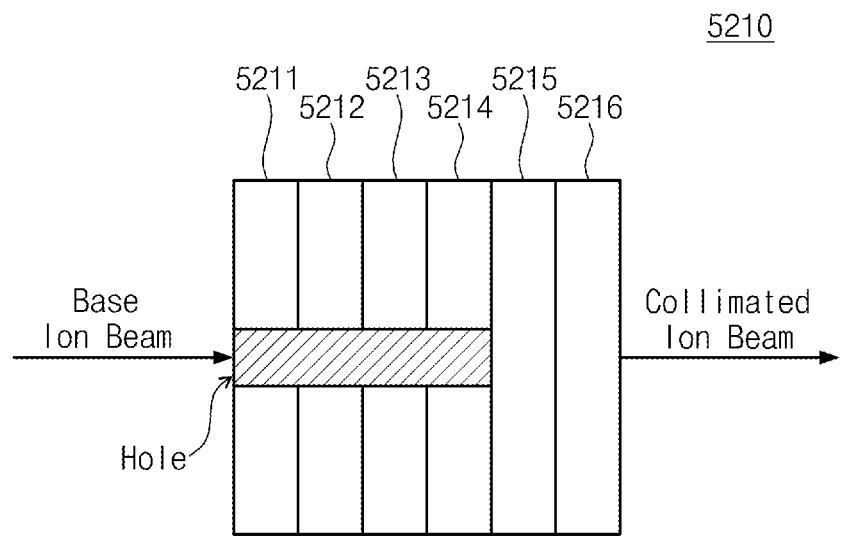
FIG. 15 is a lateral view of a scintillating module of an ion beam filter according to an embodiment of the inventive concept

FIG. 15 is a lateral view of a scintillating module of an ion beam filter according to an embodiment of the inventive concept. A scintillating module 5210 may be formed of a plurality of scintillating layers 5211 to 5216 which are stacked. In example embodiments, there is illustrated an example in which six scintillating layers are stacked. However, the inventive concept is not limited thereto.

The scintillating layers 5211 to 5216 may include a plurality of scintillators arranged in line. Like the above-described scintillating module 3210 of an ion beam profiler 3200 (refer to FIG. 12), scintillators included in each of the scintillating layers 111 to 114 may extend in a direction being at right angles to scintillators included in adjacent scintillating layers.

An ion beam incident onto a scintillator may cause Compton scattering via collision with atoms of the scintillator. With the Compton scattering, recoilelectron may be generated when the ion beam collides with outer electrons of an atom included in a scintillator.

The recoilelectron may have various kinetic energies according to energy and progress direction of an input ion beam. The recoilelectron may do electrical reaction with another atom on a progress course. The recoilelectron may lose the kinetic energy by the electrical reaction and generate light via combination with an ionized atom. That is, a scintillator may convert an input ion beam into light. A detector may output a photoelectron by collecting light generated from scintillators.

In example embodiments, cross sections of scintillators may be illustrated to be square. However, the inventive concept is not limited thereto. For example, cross sections of scintillators may be formed to have various shapes including a circle, a regular hexagon, and a regular triangle.

Like a scintillating module 3210 of an ion beam profiler 3200, the scintillating module 5210 may monitor energy distribution and progress course of an ion beam using a plurality of scintillating layers 5211 to 521n. The ion beam filter 5200 may provide a monitoring result to a user or feed it back to the ion beam generator.

Meanwhile, unlike the scintillating module 3210, a hole may be formed at the scintillating module 5210. A length of the scintillating module 5210 which the ion beam penetrates may vary responsive to a length of the hole of the scintillating module 5210.

The ion beam may penetrate scintillating layers 5211 to 5216 included in the scintillating module 5210. The ion beam may lose energy due to collision whenever it passes through each scintillating layer. Energy which the ion beam loses may be converted into light by Compton scattering as described above.

If a length of the scintillating module 5210 which the ion beam penetrates varies, energy of an ion beam output from the scintillating module 5210 may vary. Energy of an ion beam output from the scintillating module 5210 may be adjusted to a specific energy band by forming holes at a part of scintillating layers.

Referring to FIG. 15, a base ion beam generated from an ion beam generator may pass through a hole formed from an incidence surface side of the scintillating module 5210. The base ion beam may lose energy over passing through the scintillating module 5210, so that it is focused to a collimated ion beam having a specific energy band. The ion beam filter may generate the collimated ion beam having a specific energy band from the base ion beam using a hole formed at the scintillating module 5210.

Figure 16:
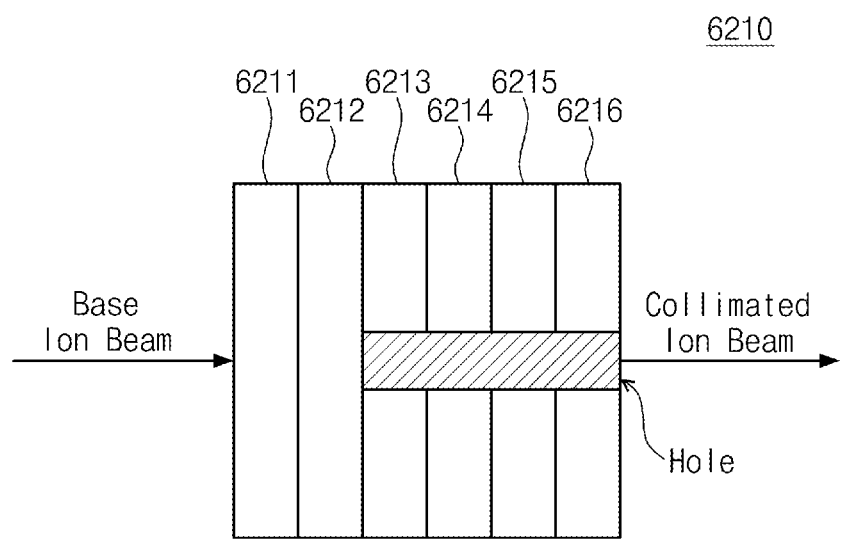
FIG. 16 is a lateral view of a scintillating module according to still another embodiment of the inventive concept.

FIG. 16 is a lateral view of a scintillating module according to still another embodiment of the inventive concept. Referring to FIG. 16, a base ion beam generated from an ion beam generator may pass through a hole formed from an output surface side of a scintillating module 6210. The base ion beam may lose energy over passing through the scintillating module 6210, so that it is focused to a collimated ion beam having a specific energy band. The ion beam filter may generate the collimated ion beam having a specific energy band from the base ion beam using a hole formed at the scintillating module 6210.

Figure 17:
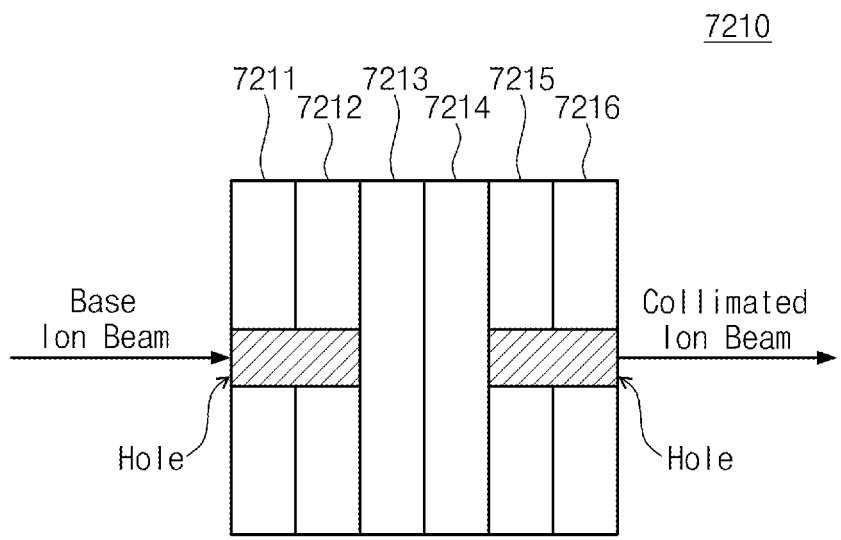
FIG. 17 is a lateral view of a scintillating module according to still another embodiment of the inventive concept.

FIG. 17 is a lateral view of a scintillating module according to still another embodiment of the inventive concept. Referring to FIG. 17, a base ion beam generated from an ion beam generator may pass through a hole formed from input and output surface sides of a scintillating module 7210. The base ion beam may lose energy over passing through the scintillating module 7210, so that it is focused to a collimated ion beam having a specific energy band. The ion beam filter may generate the collimated ion beam having a specific energy band from the base ion beam using a hole formed at the scintillating module 7210.

Figure 18:
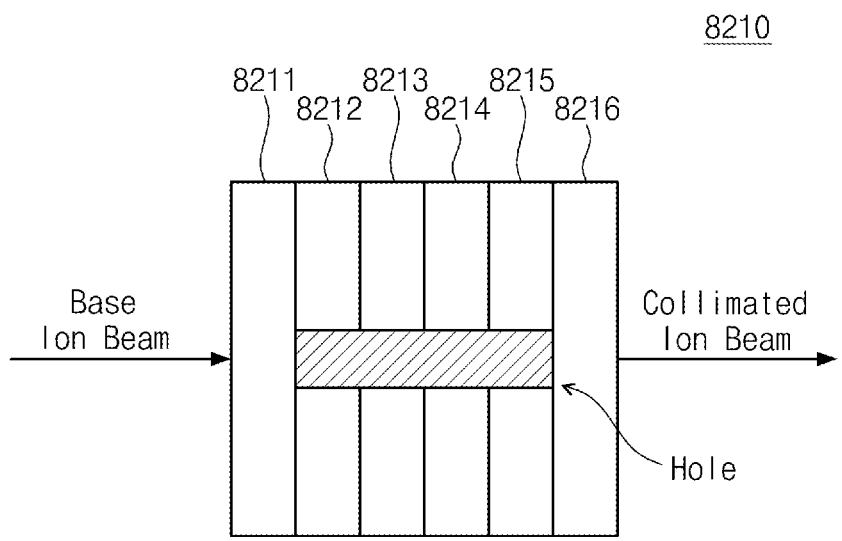
FIG. 18 is a lateral view of a scintillating module according to still another embodiment of the inventive concept.

FIG. 18 is a lateral view of a scintillating module according to still another embodiment of the inventive concept. Referring to FIG. 18, a base ion beam generated from an ion beam generator may pass through a hole formed inside a scintillating module 8210. For example, a plurality of holes may be formed inside the scintillating module 8210.

The base ion beam may lose energy over passing through the scintillating module 8210, so that it is focused to a collimated ion beam having a specific energy band. The ion beam filter may generate the collimated ion beam having a specific energy band from the base ion beam using a hole formed at the scintillating module 8210.

With the inventive concept, a scintillating module and a PET system using the same may have improved resolution. An ion beam profiler of the inventive concept may measure an energy distribution of an ion beam in real time. Also, an ion beam filter of the inventive concept may transmit an ion beam having a required energy band using a measured energy distribution. Thus, with the ion beam profiler, the ion beam filter, and an ion beam generating device using the same, it is possible to obtain the high accuracy by providing an ion beam having a required energy band in real time.

The inventive concept may be modified or changed variously. For example, an ion beam generator, a scintillating module, a photoelectric conversion module, and an analysis module may be changed or modified variously according to environment and use.

While the inventive concept has been described with reference to exemplary embodiments, it will be apparent to those skilled in the art that various changes and modifications may be made without departing from the spirit and scope of the present invention. Therefore, it should be understood that the above embodiments are not limiting, but illustrative.

What is claimed is:

1. A scintillating module comprising:
   a first scintillating layer including a plurality of scintillators extending in a first direction;
   a second scintillating layer including a plurality of scintillators extending in a second direction and stacked in a third direction with respect to the first scintillating layer, and
   at least one hole penetrating the first and second scintillating layers,
   wherein the first, second and third directions are orthogonal to each other.

2. The scintillating module of claim 1, wherein outer walls of the plurality of scintillators totally reflect gamma rays.

3. The scintillating module of claim 1, wherein the first scintillating layer includes a plurality of detectors which are configured to collect light generated from the plurality of scintillators of the first scintillating layer and to output photoelectrons using the collected light.

4. The scintillating module of claim 1, wherein the plurality of scintillators has a triangular structure, a square pillar structure, a hexagonal structure, or a cylindrical structure.

5. The scintillating module of claim 1, wherein a depth direction of the hole is aligned with an input direction of an ion beam.

6. An ion beam filter comprising:
   a scintillating module which generates light in response to a base ion beam and provides a collimated ion beam using the base ion beam;
   a photoelectric conversion module which converts the light into an electrical pulse; and an analysis module which calculates energy distribution and progress course of the collimated ion beam, wherein the scintillating module includes a plurality of scintillating layers stacked and at least one hole, the plurality of scintillating layers extends in a direction and includes a plurality of scintillators to generate the light in response to the ion beam, extending directions of scintillators included in adjacent scintillating layers are orthogonal each other, and an energy distribution of the collimated ion beam determined based on the hole.

7. The ion beam filter of claim 6, wherein the hole is formed from an incidence surface side of the scintillating module.

8. The ion beam filter of claim 6, wherein the hole is formed from an output surface side of the scintillating module.

9. The ion beam filter of claim 6, wherein the hole is formed inside the scintillating module.

10. The ion beam filter of claim 6, wherein the energy distribution of the collimated ion beam is determined based on a sum of a length of the at least one hole.

11. The ion beam filter of claim 6, wherein a depth direction of the hole is aligned with an output direction of the collimated ion beam.

12. An ion beam generating device comprising:
an ion beam generator which generates a base ion beam by accelerating ions; and
an ion beam filter which provides a collimated ion beam using the base ion beam,
wherein the ion beam filter comprises:
a scintillating module which generates light in response to a base ion beam and provides a collimated ion beam using the base ion beam;
a photoelectric conversion module which converts the light into an electrical pulse; and
an analysis module which calculates energy distribution and a progress course of the collimated ion beam,
wherein the scintillating module includes a plurality of stacked scintillating layers and at least one hole, the plurality of scintillating layers extends in a direction and includes a plurality of scintillators that generate the light in response to the ion beam, extending directions of scintillators included in adjacent scintillating layers are orthogonal each other, and an energy distribution of the collimated ion beam is calculated based on the hole.

13. The ion beam generating device of claim 12, wherein the ion beam generator comprises:
a pulse laser which generates an ultra-short pulse laser;
a pulse stretcher which stretches a pulse width of the ultra-short pulse laser;
a pulse selector which selects a specific pulse of the stretched pulse laser;
an amplifier which amplifies a magnitude of the selected pulse; and
a pulse compressor which compresses a pulse width of the amplified pulse.

14. The ion beam generating device of claim 13, wherein the pulse selector includes a pockels cell.

15. The ion beam generating device of claim 12, wherein a depth direction of the hole is aligned with an output direction of the collimated ion beam.

* * * * *